United States Patent [19]

Halczenko et al.

[11] Patent Number: 4,587,253

[45] Date of Patent: May 6, 1986

[54] BRIDGED PYRIDINE COMPOUNDS USEFUL AS CALCIUM CHANNEL BLOCKERS AND ANALGESICS

[75] Inventors: Wasyl Halczenko, Hatfield; George D. Hartman, Lansdale, both of Pa.

[73] Assignee: Merck & Co., Inc., Rahway, N.J.

[21] Appl. No.: 635,971

[22] Filed: Jul. 30, 1984

[51] Int. Cl.$^4$ .................. A61K 31/44; A61K 31/47; C07D 221/22
[52] U.S. Cl. .................. 514/289; 514/222; 514/236; 514/253; 514/279; 514/280; 514/281; 514/282; 514/284; 514/286; 544/61; 544/125; 544/361; 546/39; 546/40; 546/43; 546/44; 546/63; 546/74
[58] Field of Search .................. 546/39, 40, 43, 44, 546/63, 74; 544/61, 125, 361; 514/222, 236, 253, 279, 280, 281, 282, 284, 286

[56] References Cited

U.S. PATENT DOCUMENTS

| | | | |
|---|---|---|---|
| 3,466,288 | 9/1969 | Hansen et al. | 546/74 X |
| 3,518,271 | 6/1970 | Shavel Jr. et al. | 546/43 |
| 4,172,201 | 10/1979 | Jarque et al. | 546/63 |
| 4,178,450 | 12/1979 | Jarque et al. | 546/63 |
| 4,532,237 | 7/1985 | Hartman et al. | 514/226 |
| 4,548,941 | 10/1985 | Halczenko et al. | 514/295 |

OTHER PUBLICATIONS

Bossert, et al. Angew, Chem. Int. Ed., vol. 20, pp. 762–769 (1981).
Schramm, et al., Nature, vol. 309, pp. 535–537, (Jun. 9, 1983).

*Primary Examiner*—Donald G. Daus
*Assistant Examiner*—Diana G. Rivers
*Attorney, Agent, or Firm*—Salvatore C. Mitri; Michael C. Sudol

[57] ABSTRACT

Novel substituted and bridged pyridine compounds useful as calcium channel blockers and analgesics, pharmaceutical compositions thereof, and methods of treatment are disclosed.

13 Claims, No Drawings

BRIDGED PYRIDINE COMPOUNDS USEFUL AS CALCIUM CHANNEL BLOCKERS AND ANALGESICS

BACKGROUND OF THE INVENTION

The pharmacological function and importance of calcium antagonists, or calcium channel blockers, is well known and has been extensively reported in the literature [see; e.g., P. D. Henry, "Comparative Pharmacology of Calcium Antagonists: Nifedipine, Verapamil and Diltiazem", *The American Journal of cardiology*, 46, 1047-1058 (1980); K. H. Dangman, et al., "Effects of Nifedipine on Electrical Activity of Cardiac Cells", *The American Journal of Cardiology*, 46, 1061-1067 (1980); E. Braunwald, "Introduction: Calcium Channel Blockers", *The American Journal of Cardiology*, 46, 1045 (1980); L. D. Hillis, "The New Coronary Vasodilators: Calcium Blockers", *J. Card. Med.*, 5(6), 583 (1980); M. J. Berridge, "Receptors and Calcium Signalling", *Trends in Pharmacological Sciences* 1, 419, (1980); W. G. Nayler, et al., "Calcium Antagonists: definition and mode of action", *Basic Research in Cardiology*, 76, No. 1, 1-15 (1981)].

Weller et al., [*J. Org. Chem.*, 48, pp. 3061-7 (1983)]disclose 1'-methylspiro [benzofuran-3(2H),4'-piperidine]as a substructure of morphine which is an early intermediate in a general synthesis of morphine but not possessing exceptional analgesic activity. Weller et al. also teach the preparation of spiro[benzofuran-3(2H),4'(1'H)-pyridines]as potential intermediates in a synthesis of morphine but no biological activity of these compounds is reported.

Goldman [Angew. Chem. Int. Ed. Engl., 20, pp. 779-780 (1981)]teaches the preparation of spiro[benzothiophene-1-oxide,4'-pyridines]as an intermediate in the preparation of 4,4-disubstituted 1,4-dihydropyridines.

SUMMARY OF THE INVENTION

This invention is directed to novel substituted and bridged pyridines and derivatives thereof and to methods for preparing such compounds. This invention is also directed to pharmaceutical compositions. Methods of treatment for cardiovascular disorders in which high cellular concentration of $Ca^{++}$ is a factor and for disorders in which an analgesic would be desirable are disclosed.

DETAILED DESCRIPTION OF THE INVENTION

The specific substituted and bridged pyridine compounds of this invention are represented by the following general structural formulae (I) and (II):

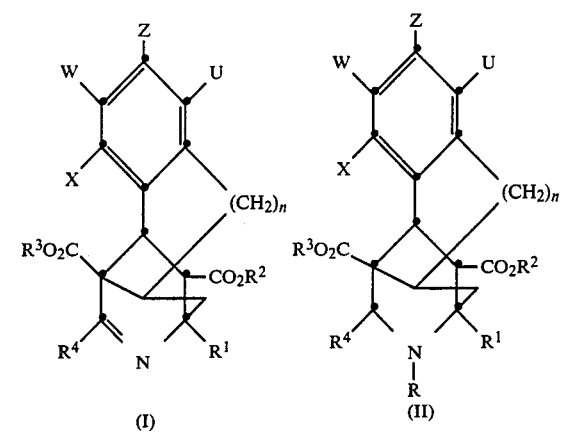

wherein:
n is 0, 1 or 2;
R is hydrogen or $C_1$–$C_8$ alkyl;
$R^1$ and $R^4$ independently are hydrogen, $C_1$–$C_8$ alkyl, $C_2$–$C_8$ alkenyl, $C_3$–$C_8$ cycloalkyl, $C_1$–$C_8$ hydroxyalkyl;
$R^2$ and $R^3$ independently are $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy (alkoxy alkyl), $C_1$–$C_8$ aminoalkyl wherein the amino group is $NR^5R^6$ in which $R^5$ and $R^6$ independently are hydrogen, $C_1$–$C_8$ alkyl, $C_7$–$C_{14}$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or N'-$C_1$-$C_4$-alkylpiperazinyl; and
X, W, Z and U independently are hydrogen, $C_1$–$C_8$ alkyl $C_1$–$C_8$ alkoxy, $CF_3$, cyano, nitro or halo (such as chloro, bromo or fluoro), provided that at least two of X, W, Z and U are hydrogen or X and W or W and Z or Z and U together with the phenyl group to which they are attached form a naphthyl or benzoxadiazole group, and pharmaceutically acceptable salts thereof.

The preferred compounds of this invention are those represented by the general structural formulae (I) and (II) wherein:
n is 0 or 1;
R is hydrogen or $C_1$–$C_8$ alkyl;
$R^1$ and $R^4$ independently are hydrogen or $C_1$–$C_8$ alkyl;
$R^2$ and $R^3$ independently are $C_1$–$C_8$ alkyl;
X, W, Z and U independently are hydrogen, $C_1$–$C_8$ alkoxy, $CF_3$, cyano, nitro or halo provided that at least two of X, W, Z and U are hydrogen.

The most preferred compounds of this invention are those preferred compounds wherein X, W, Z and U are hydrogen.

The compounds of this invention possess asymmetric centers and thus may exist in different isomeric forms. All such forms are included within the scope of this invention. Specifically, the compounds of the formulae (I) and (II) have an asymmetric center at the carbon atom to which the ester moiety, $—CO_2R^2$, is attached. Whenever that ester moiety is below the plane of the piperidine ring (i.e., down), that stereochemical configuration is denoted as the alpha (α)-isomer. Similarly, whenever that ester moiety is above the plane of the piperidine ring (i.e. up), that stereochemical configuration is denoted as the beta (β)-isomer. The compounds of the formula (II) contain an additional asymmetric center at the carbon atom to which the radical $R^4$, when $R^4$ is not hydrogen, is attached. Separation of the individual isomers is accomplished by standard procedures known in the art.

Illustrative of the compounds of this invention are the following compounds of the formula (I) which are the α-isomers, the β-isomers or mixtures thereof:

(1) Dimethyl 4,4a,9,9a-tetrahydro-1,3-dimethyl-3,9-methano-3H-indeno[2,1-c]pyridine-9a,10-dicarboxylate [Formula (I) where n is O, $R^1$, $R^2$, $R^3$, $R^4$ are methyl and X, W, Z and U are hydrogen];

(2) Dimethyl 4,4a,9,9a-tetrahydro-1,3-dimethyl-3,9-methano-7-nitro-3H-indeno[2,1-c]pyridine-9a,10-dicarboxylate [Formula (I) where n is O, $R^1$, $R^2$, $R^3$ and $R^4$ are methyl, W is nitro and X, Z and U are hydrogen];

(3) Dimethyl 3,4,4a,5,10α,10a-hexahydro-1,3α-dimethyl-3,10-methanobenzo[g]isoquinoline-10aα,11β-dicarboxylate [Formula (I) where n is 1, $R^1$, $R^2$, $R^3$ and $R^4$ are methyl and X, W, Z and U are hydrogen]; and (4) Dimethyl 7,7a,10,11,11a,12-hexahydro-8,10α-dimethyl-7,10-methanonaphth[1,2-g]isoquinoline-7aα,13β-dicarboxylate [Formula (I) where n is 1, $R^1$, $R^2$, $R^3$ and $R^4$ are methyl, U and Z together are —CH=CH—CH=CH— and X and W are hydrogen].

Also illustrative of the compounds of this invention are the following compounds of the formula (II) which are the individual stereoisomers or mixtures thereof:

(1) Dimethyl 2,3,4,4a,9,9a-hexahydro-1,3-dimethyl-3,9-methano-1H-indeno[2,1-c]pyridine-9a,10-dicarboxylate [Formula (II) where n is O, R is hydrogen, $R^1$, $R^2$, $R^3$, $R^4$ are methyl and X, W, Z and U are hydrogen];

(2) Dimethyl 2,3,4,4a,9,9a-hexahydro-1,2,3-trimethyl-3,9-methano-1H-indeno[2,1-c]pyridine-9a,10-dicarboxylate [Formula (II) where n is O, R, $R^1$, $R^2$, $R^3$ and $R^4$ are methyl and X, W, Z and U are hydrogen];

(3) Dimethyl 1,2,3,4,4a,5,10,10a-octahydro-1,3-dimethyl-3,10-methanobenzo[g]isoquinoline-10a,11-dicarboxylate [Formula (II) where n is 1, R is hydrogen, $R^1$, $R^2$, $R^3$ and $R^4$ are methyl and X, W, Z and U are hydrogen]; and (4) Dimethyl 7,7a,8α,9,10,11,11a,12-octahydro-8,10-dimethyl-7,10-methanonaphth[1,2-]isoquinoline-7a,13-dicarboxylate [Formula (II) where n is 1, R is hydrogen, $R^1$, $R^2$, $R^3$ and $R^4$ are methyl, U and Z together are —CH=CH—CH=CH— and X and W are hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic, and trichloroacetic, acetic, glycolic, pamoic, pyruvic, malonic, succinic, maleic, fumaric, malic, tartaric, citric, mandelic, benzoic, cinnamic, methanesulfonic, ethanesulfonic, salicylic, p-toluenesulfonic, cyclohexanesulfamic, and the like and include acids related to the pharmaceutically acceptable salts listed in Journal of Pharmaceutical Science, 66, 2 (1977) and incorporated herein by reference. Note that for the compounds of formula (I) strong acids are required to form the pharmaceutically acceptable salts.

The compounds of the formula (I) are conveniently prepared from known or readily available starting materials utilizing the general synthetic pathway described below:

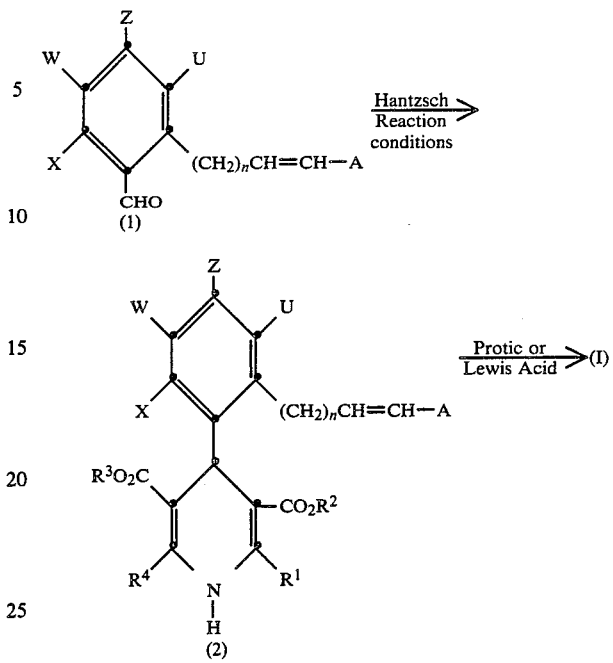

The aryl aldehyde (1), wherein n, X, W, Z and U are described above and A is hydrogen or a trialkylsilyl radical, is reacted with an appropriately substituted 3-aminopropenoate, such as methyl 3-aminocrotonate, and an appropriately substituted 3-oxo-propanoate, such as methyl acetoacetate, under the general Hantzsch reaction conditions to afford the aryl dihydropyridine compound (2).

The aryl dihydropyridine (2) is then treated at −10° to 50° C., preferably ambient temperature, with between 0.5 and 5.0 equivalents, preferably 1.0 equivalents, of either a protic acid or a Lewis acid in an inert solvent to yield the compound of Formula (I). Examples of such protic acids and Lewis acids include gaseous hydrogen chloride, gaseous hydrogen bromide, titanium tetrachloride, trimethylsilyl trifluoromethanesulfonate and tin tetrachloride.

The compounds of the formula (II) wherein R is hydrogen are conveniently prepared from the compounds of Formula (I) by catalytically reducing the double bond or by treatment with a reducing agent, such as sodium borohydride, lithium aluminum hydride or diisobutylaluminum hydride in an inert solvent. The compounds of the formula (II) wherein R is $C_1$–$C_8$ alkyl are obtained by alkylating under standard conditions the compounds of the formula (II) wherein R is hydrogen.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendepine from membrane.

A number of compounds of the present invention were found to inhibit in vitro the contraction of isolated guinea pig ileum produced by electrical stimulation and would be useful for disorders in which an analgesic would be desireable, such as the treatment of pain and inflammation. The specific compounds useful as an analgesic include:

(a) dimethyl 1,2,3,4,4a,5,10,10a-octahydro-1,3$\alpha$-dimethyl-3,10-methanobenzo(g)-isoquinoline-10a$\alpha$,11-dicarboxylate;

(b) dimethyl 7,7a,10,11,11a,12,-hexahydro-8,10$\alpha$-dimethyl-7,10-methanonaphth[1,2-g]isoquinoline-7a$\alpha$,13$\beta$-dicarboxylate and (c) dimethyl 2,3,4,4a,9,9a-hexahydro-1,3-dimethyl-3,9-methano-3H-indeno[2,1-c]pyridine-9a,10$\alpha$-dicarboxylate.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or $\beta$-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for preparing the compounds of this invention, but are not to be construed as limiting this invention in any manner.

EXAMPLE 1

Preparation of Dimethyl 4,4a,9,9a-tetrahydro-1,3-dimethyl-3,9-methano-3H-indeno[2,1-c]pyridine-9a,10-dicarboxylate (a) 2-(2-Trimethylsilylethenyl)benzaldehyde (1a)

To a solution of bis(trimethylsilyl)methane (10 mmol) in tetrahydrofuran/hexamethylphosphorous triamide (4:1 20 ml) under nitrogen at $-75°$ C. was added n-butyllithium and the solution stirred at $-40°$ to $-50°$ C. for 6 hours. The solution was cooled to $-75°$ C. and 2-[2-(1,3-dioxalanyl)]benzaldehyde (10 mmol) in tetrahydrofuran (10 ml) was added dropwise and the reaction mixture slowly warmed to ambient temperature over 16 hours. To the reaction mixture was added saturated ammonium chloride (10 ml) and then water (10 ml) and diethyl ether (75 ml). The phases were separated and the aqueous phase re-extracted with diethyl ether (2×25 ml). The combined organic phases were washed with brine (25 ml), dried over anhydrous sodium sulfate and filtered. The filtrate was concentrated in vacuo to yield a yellow oil which was flash chromatographed on silica gel eluted with hexane:ethyl acetate (96:4) to afford the desired acetal as a clear oil. The acetal (1.45 g) was dissolved in acetone (30 ml) and treated with p-toluenesulfonic acid at ambient temperature for 6 hours. This material was flash chromatographed on silica gel eluted with hexane:ethyl acetate (98:2) to afford Compound 1a as a clear oil.

(b) Dimethyl 2,5-dimethyl-4-[2-(2-trimethylsilylethenyl)phenyl]-1,4-dihydropyridine-3,5-dicarboxylate (1b)

To the Compound 1a (3.1 mmol) in anhydrous methanol (8 ml) was added methyl 3-aminocrotonate (3.1 mmol) and methyl acetoacetate (3.1 mmol) and the resulting solution heated at reflux under nitrogen for 5 days. The solvent was removed in vacuo to yield a yellow oil which was purified by flash chromatography on silica gel eluted with hexane:diethyl ether (1:1) to afford Compound 1b as yellowish powder ($R_f=0.3$, m.p. 148°–150° C.).

(c) Dimethyl 4,4a,9,9a-tetrahydro-1,3-dimethyl-3,9-methano-3H-indeno[2,1-c]pyridine-9a,10-dicarboxylate To the Compound 1b (1.0 mmol) in Chloroform (10 ml) was added titanium tetrachloride (1.1 mmol) under nitrogen at ambient temperature. After 3 hours, the solvent was removed in vacuo and the residue flash chromatographed on silica gel eluted with hexane:diethyl ether (1:2) to afford the desired product. The $\beta$-isomer was a white solid ($R_f=0.4$, m.p. 104.5°–105.5°

C.). The α-isomer was a white solid ($R_f$=0.3, m.p. 160°–161.5° C.).

EXAMPLE 2

Alternate Preparation of Dimethyl 4,4a,9,9a-tetrahydro-1,3-dimethyl-3,4-methano-3H-indeno[2,1-c]pyridine-9a,10-dicarboxylate

(a) 2-Ethenylbenzaldehyde (2a)

To a solution of 2-bromostyrene (115 mmol) in dry tetrahydrofuran (200 ml) at −65° C. under nitrogen was added dropwise n-butyllithium (115 mmol) in hexane. The reaction mixture was stirred at −65° C. for an additional hour and a solution of N-formylpiperidine (125 mmol) in tetrahydrofuran (50 ml) was added dropwise. The reaction mixture was allowed to warm to ambient temperature overnight. The reaction mixture was cooled to 0° C. and then quenched with saturated ammonium chloride (50 ml). The reaction mixture was extracted with diethyl ether (2×50 ml) and the combined organic phases were washed with 3N hydrochloric acid (2×50 ml), saturated aqueous sodium bicarbonate (50 ml), and brine, dried over anhydrous sodium sulfate and filtered. The filtrate was concentrated in vacuo to yield the Compound 2a which was directly used in the next reaction.

(b) Dimethyl 2,6-dimethyl-4-(2-ethenylphenyl)-1,4-dihydropyridine-3,5-dicarboxylate (2b)

To the Compound 2a (106 mmol) in anhydrous methanol (100 ml) was added methyl 3-aminocrotonate (106 mmol) and methyl acetoacetate (106 mmol) and the resulting solution heated at reflux under nitrogen for 4 days. The solvent was removed in vacuo to give a viscous yellow oil which was diluted in diethyl ether (75 ml) and then hexane (50 ml). After stirring overnight, a yellow solid was collected by filtration and purified by flash chromatography on silica gel eluted with hexane:diethyl ether (1:2) to give Compound 2b as a yellow solid ($R_f$=0.4, m.p. 140°–148°).

(c) Dimethyl 4,4a,9,9a-tetrahydro-1,3-dimethyl-3,9-methano-3H-indeno[2,1-c]pyridine-9a,10-dicarboxylate Into a solution of the Compound 2b (0.3 mmol) in dry chloroform (5 ml) was bubbled anhydrous hydrogen chloride. The resulting solution was stirred for 2.5 hours at ambient temperature. The reaction mixture was diluted chloroform (10 ml) and water (5 ml) and then neutralized with concentrated aqueous ammonium hydroxide. The organic phase was separated and the aqueous phase extracted with chloroform (2×20 ml). The combined organic phases were washed with brine, dried over anhydrous sodium sulfate and filtered. The solvent was removed in vacuo and the resulting yellow oil purified by flash chromatography on silica gel eluted with hexane:diethyl ether (1:2). The β-isomer had an $R_f$=0.4 and the α-isomer had an $R_f$=0.3.

EXAMPLE 3

Preparation of Dimethyl 3,4,4a,5,10α,10a-hexahydro-1,3α-dimethyl-3,10-methanobenzo(g)isoquinoline-10aα,11-dicarboxylate

(a) 1-[2-(1,3-Dioxalanyl)]-2-[1-(trimethylsilyl)-propen-3-yl]benzene (3a)

To magnesium turnings (11 mmol) under nitrogen and dry tetrahydrofuran was added a small portion (2 ml) of a solution of 2-bromoethenyltrimethylsilane (10 mmol) in dry tetrahydrofuran (10 ml) and the reaction initiated with slight heating. The remainder of the solution was added dropwise at reflux and heated to reflux for an additional hour. The reaction mixture was cooled to ambient temperature, cuprous iodide (9.8 mmol) was added, the reaction mixture cooled to 0° C. and 2-[2-(1,3-dioxalanyl)]-1-bromomethylbenzene (9.8 mmol) in tetrahydrofuran (10 ml) was added dropwise. After 45 minutes the reaction was quenched at 0° C. with saturated aqueous ammonium chloride (10 ml) and then water (10 ml). The reaction mixture was extracted with diethyl ether (3×50 ml) and the combined organic phases were washed with brine, dried over anhydrous sodium sulfate, filtered and concentrated in vacuo to give an oil. The oil was purified by flash chromatography on silica gel eluted with ethyl acetate:hexane (98:2) to afford the Compound 3a as an oil ($R_f$=0.4).

(b) 2-(1-Trimethylsilylpropen-3-yl)-benzaldehyde (3b)

To the Compound 3a (24 mmol) in dry acetone (100 ml) was added p-toluenesulfonic acid monohydrate and the resultant solution allowed to stand at ambient temperature for 3 days. The solvent was removed in vacuo and the residue diluted with diethyl ether (50 ml), washed with dilute sodium bicarbonate, brine, dried over anhydrous sodium sulfate and filtered. The filtrate was concentrated in vacuo to yield an oil which was purified by flash chromatography on silica gel eluted with ethyl acetate:hexane (95:5) to afford the Compound 3b as an oil ($R_f$=0.5).

(c) Dimethyl 2,6-dimethyl-4-[2-[1-(trimethylsilylpropen-3-yl)]phenyl]-1,4-dihydropyridine-3,5-dicarboxylate (3c)

To the Compound 3b (50 mmol) in dry methanol (50 ml) was added methyl 3-aminocrotonate (50 mmol) and methyl acetoacetate (50 mmol) and the resulting solution heated at reflux under nitrogen for 3 days. After the solvent was removed, the resulting oil was triturated with hexane to afford the Compound 3c as a white solid (m.p. 92°–98° C.).

(d) Dimethyl 3,4,4a,5,10α,10a-hexahydro-1,3α-dimethyl-3,10-methanobenzo[g]isoquinoline10aα,11-dicarboxylate To the Compound 3c (0.2 mmol) in methylene chloride (3 ml) under nitrogen at ambient temperature was added titanium tetrachloride (0.6 mmol) and the reaction mixture allowed to stand for 16 hours. The solvent was removed in vacuo and the residue purified by flash chromatography on silica gel eluted with methanol:chloroform (1:99) to afford the β-isomer ($R_f$=0.4, m.p. 96°–107° C.) and the α-isomer ($R_f$=0.3, m.p. 150°–152° C.).

EXAMPLE 4

Preparation of Dimethyl 7,7a,10,11,11a,12-hexahydro8,10α-dimethyl-7,10-methanonaphth[1,2-g]-isoquinoline-7aβ,13-dicarboxylate (a) Dimethyl 2,6-dimethyl-4-[2-(1-[3-propenyl]naphthyl]-1,4-dihydropyridine-3,5-dicarboxylate (4a)

Utilizing the general procedure of Example 1(b), 1-allyl-2-naphthalenecarboxaldehyde (1.0 mmol) methyl 3-aminocrotonate (1.0 mmol) and methyl acetoacetate (1.0 mmol) were reacted to afford the Compound 4a (m.p. 180°–183° C.).

(b) Dimethyl 7,7a,10,11,11a,12-hexahydro-8,10α-dimethyl-7,10-methanonaphth[1,2-g]isoquinoline-7aβ,13-dicarboxylate Utilizing the general procedure of Example 1(c), the Compound 4a (0.2 mmol) was reacted with titanium tetrachloride (0.6 mmol) to afford the desired product as the pure β-isomer ($R_f$=0.4, m.p. 192°–198° C.) and the pure α-isomer ($R_f$=0.3, m.p. 193°–195° C.).

EXAMPLE 5

Preparation of Dimethyl 7,7a,8α,9,10,11, 11a, 12-octahydro-8β,10α-dimethyl-7,10-methanonaphth[1,2-g]-isoquinoline-7aα,13β-dicarboxylate To the Compound 4b (0.3 mmol) dissolved in acetic acid (3 ml) was added in one portion sodium borohydride (0.35 mmol). After 30 minutes at ambient temperature with stirring under nitrogen a precipitate formed. After an additional 2 hours the reaction was quenched with water (5 ml) and the reaction mixture extracted with diethyl ether (10 ml) and the organic phase discarded. The aqueous phase was neutralized with 10N sodium hydroxide and extracted with diethyl ether (3×30 ml). The combined organic phases were washed with brine, dried over anhydrous sodium sulfate and filtered. The solvent was removed in vacuo and the residue triturated with diethyl ether to afford the desired product as a white solid (m.p. 206°–8° C.).

EXAMPLES 6–9

The following compounds of formula (II) were prepared utilizing the general procedure of Example 5:

(6) Dimethyl 1,2,3,4,4a,5,10,10a-octahydro-1,3α-dimethyl-3,10-methanobenzo[g]isoquinoline-10aα,-11β-dicarboxylate maleate (m.p. 179°–181° C.);

(7) Dimethyl 2,3,4,4a,9,9a-hexahydro-1,3-dimethyl-3,9-methano-1H-indeno[2,1-c]pyridine-9a,10α-dicarboxylate (m.p. 104°–106° C.);

(8) Dimethyl 1,2,3,4,4a,5,10,10a-octahydro-1,3-dimethyl-3,10-methanobenzo(g)isoquinoline-10a,-11α-dicarboxylate maleate (m.p. 148°–153° C.); and (9) Dimethyl 2,3,4,4a,9,9a-hexahydro-1,3-dimethyl-3,9-methano-1H-indeno[2,1-]pyridine-9a,10β-dicarboxylate maleate (m.p. 184.5°–186.5° C.).

EXAMPLE 10

Preparation of Dimethyl 2,3,4,4a,9,9a-hexahydro-1,2,3α-trimethyl-3,9-methano-1H-indeno-[2,1-c]pyridine-9a,10α-dicarboxylate To the Compound from Example 7 (0.3 mmol) in acetonitrile (3 ml) was added dimethyl sulfate (0.3 mmol) and triethylamine (0.3 mmol) and the resulting solution heated at reflux for 18 hours. The solvent was removed in vacuo and the residue dissolved in water (5 ml). The aqueous solution was extracted with diethyl ether (5×15 ml). The combined organic phases were dried over anhydrous sodium sulfate, filtered and the solvent removed to give a solid which was purified by flash chromatography on silica gel eluted with methanol:methylene chloride (25:975) to afford the desired product ($R_f$=0.5). Trituration of this product with petroleum ether yielded pure material (m.p. 171°–174° C.).

Example 11–15

The following compounds of the formula (I) are prepared by utilizing the general procedures of Examples 1 to 4:

| Compound No. | n | $R^1$ | $R^2$ | $R^3$ | $R^4$ | X | W | Z | U |
|---|---|---|---|---|---|---|---|---|---|
| 11 | 0 | Et | Me | Me | Et | H | OMe | H | H |
| 12 | 1 | Me | Me | Me | Me | H | H | $CF_3$ | H |
| 13 | 1 | Et | Et | Et | Et | H | H | $NO_2$ | H |
| 14 | 2 | $CH_2CH=CH_2$ | $CH_2CH=CH_2$ | Me | Me | H | H | H | H |
| 15 | 1 | $CH_2OH$ | Et | Et | Me | H | OMe | H | H |
| 16 | 0 | Me | Me | $CH_2OH$ | Me | H | H | Et | H |
| 17 | 2 | Et | —⟨cyclohexyl⟩ | $CH_2CH_2OH$ | Et | Me | H | H | H |
| 18 | 1 | Me | Me | $CH_2CHCH_2$<br>\|  \|<br>OHOH | Me | H | H | H | Me |
| 19 | 1 | Me | $CH_2OH$ | $CH_2CH_2OCH_2CH_2OCH_3$ | Me | H | Cl | H | H |
| 20 | 0 | Et | $CH_2NMe_2$ | $CH_2NMe_2$ | Et | Cl | H | H | H |
| 21 | 1 | Me | Me | —$CH_2N$⟨cyclohexyl⟩ | Me | H | CN | H | H |

Example 11-15-continued

The following compounds of the formula (I) are prepared by utilizing the general procedures of Examples 1 to 4:

| Compound No. | n | R¹ | R² | R³ | R⁴ | X | W | Z | U |
|---|---|---|---|---|---|---|---|---|---|
| 22 | 1 | Me | Me | —CH₂NCH₃ \| CH₂∅ | Me | H | H | H | H |

It should be noted that the preparation of compounds 15, 16, 17, 18 and 19 the hydroxylalkyl moiety is acylated with acetic anhydride prior to cyclization and then deacylated with sodium hydroxide.

EXAMPLE 23

As a specific embodiment of a composition of this invention an active ingredient, such as dimethyl 2,3,4,4a,9,9a-hexahydro-1,2,3α-trimethyl-3,9-methano-1H-indeno[2,1-c]pyridine-9a,10α-dicarboxylate, is formulated to yield 5000 compressed tablets each containing 50 mg of the active ingredient as follows:
Active ingredient: 250 grams
Starch: 70 grams
Dibasic calcium phosphate hydrous: 500 grams
Calcium stearate: 2.5 grams

What is claimed is:

1. A compound represented by the following general structural formula (I):

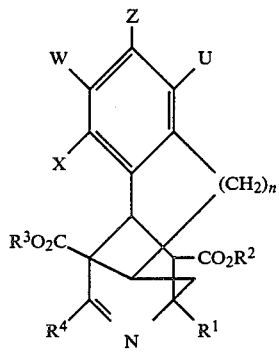

(I)

wherein:
n is 0 or 1;
R¹ and R⁴ independently are hydrogen or $C_1$-$C_8$ alkyl;
R² and R³ independently are $C_1$-$C_8$ alkyl; and
X, W, Z and U independently are hydrogen, $C_1$-$C_8$ alkoxy, $CF_3$, cyano, nitro, or halo provided that at least two of X, W, Z and U are hydrogen.

2. A compound represented by the following general structural formula (II):

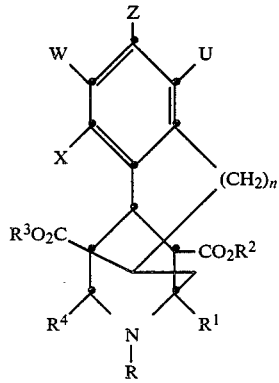

(II)

wherein:
n is 0 or 1;
R is hydrogen or $C_1$-$C_8$ alkyl;
R¹ and R⁴ independently are hydrogen or $C_1$-$C_8$ alkyl;
R² and R³ independently are $C_1$-$C_8$ alkyl; and X, W, Z and U independently are hydrogen, $C_1$-$C_8$ alkoxy, $CF_3$, cyano, nitro or halo provided that at least two of X, W, Z and U are hydrogen.

3. A compound according to claim 1 wherein: X, W, Z and U are hydrogen.

4. A compound according to claim 3 which is dimethyl 3,4,4a,5,10α,10a-hexahydro-1,3α-dimethyl-3,10-methanobenzo[g]isoquinoline-10aα,11β,-dicarboxylate.

5. A compound according to claim 1 which is dimethyl 7,7a,10,11,11a,12-hexahydro-8,10α-dimethyl-7,10-methanonaphth[1,2-g]isoquinoline-7aβ,13β-dicarboxylate.

6. A compound according to claim 2 wherein: X, W, Z and U are hydrogen.

7. A compound according to claim 6 which is dimethyl 2,3,4,4a,9,9a-hexahydro-1,2,3α-trimethyl-3,9-methano-1H-indeno[2,1-c]pyridine-9a,10α-dicarboxylate.

8. A compound according to claim 6 which is dimethyl 7,7a,8α,9,10,11,11a,12-octahydro-8β,10α-dimethyl-7,10-methanonaphth[1,2-g]isoquinoline-7aα,13β-dicarboxylate.

9. A compound according to claim 6 which is dimethyl 1,2,3,4,4a,5,10,10a-octahydro-1,3-dimethyl-3,10-methanobenzo[g]isoquinoline-10aα,11α-dicarboxylate maleate.

10. A compound according to claim 6 which is dimethyl 2,3,4,4a,9,9a-hexahydro-1,3-dimethyl-3,9-methano-1H-indenol[2,1-c]pyridine-9a,10α-dicarboxylate.

11. A pharmaceutical composition useful in the treatment of cardiovascular disorders in which a high cellular concentration of $Ca^{++}$ is a factor comprising a nontoxic therapeutically effective amount of a compound according to claim 1 or 2 in an admixture with a pharmaceutically acceptable carrier.

12. A method of treatment for cardiovascular disorders in which a high cellular concentration of $Ca^{++}$ is a factor which comprises administering to a subject in need of such treatment a nontoxic therapeutically effective amount of a compound according to claim 1 or 2.

13. A method of treatment for disorders in which an analgesic would be desirable which comprises administering to a subject in need of such treatment a nontoxic therapeutically acceptable amount of a compound selected from the group consisting of:

(a) dimethyl 1,2,3,4,4a,5,10,10a-octahydro-1,3-dimethyl-3,10-methanobenzo[g]-isoquinoline-10aα,11α-dicarboxylate maleate;

(b) dimethyl 7,7a,10,11,11a,12-hexahydro-8β,10α-dimethyl-7,10-methanonaphth[1,2-g]isoquinoline-7aα,13β-dicarboxylate; or (c) dimethyl 2,3,4,4a,9,9a-hexahydro-1,3-dimethyl-3,9-methano-1H-indeno[2,1-c]pyridine-9a,10α dicarboxylate.

* * * * *